(12) United States Patent
Shaw

(10) Patent No.: US 6,308,712 B1
(45) Date of Patent: Oct. 30, 2001

(54) IMMOBILIZING APPARATUS HAVING A STERILE INSERT

(76) Inventor: Fredrick C. Shaw, 410 Moonmist Cir., Yazoo City, MS (US) 39194

( * ) Notice: Subject to any disclaimer, the term of this patent is extended or adjusted under 35 U.S.C. 154(b) by 0 days.

(21) Appl. No.: 09/602,507

(22) Filed: Jun. 23, 2000

(51) Int. Cl.[7] .................................................. A61B 19/00
(52) U.S. Cl. .................... 128/869; 128/845; 128/846; 5/621; 5/624
(58) Field of Search .................................. 128/845, 846, 128/869, 870; 5/621, 624, 632, 652, 655, 657; 606/237, 240

(56) References Cited

U.S. PATENT DOCUMENTS

| | | |
|---|---|---|
| D. 168,139 | 11/1952 | Brady . |
| 2,765,480 | 10/1956 | Mueller . |
| 3,251,075 | 5/1966 | Saltness et al. . |
| 3,680,917 | 8/1972 | Harris . |
| 4,259,757 | 4/1981 | Watson . |
| 4,274,673 | 6/1981 | Kifferstein . |
| 4,584,730 | 4/1986 | Rajan . |
| 4,597,386 | 7/1986 | Goldstein . |
| 5,014,375 | 5/1991 | Coonrad et al. . |
| 5,096,173 | 3/1992 | Yamashita et al. . |
| 5,113,875 | 5/1992 | Bennett . |
| 5,180,386 | 1/1993 | Kennedy, Jr. . |
| 5,189,748 | 3/1993 | Garrison et al. . |
| 5,201,761 | 4/1993 | Serola . |
| 5,289,603 | 3/1994 | Kumagai . |
| 5,357,982 | 10/1994 | Shaw . |
| 5,584,302 | 12/1996 | Sillaway et al. . |
| 5,727,266 | 3/1998 | Pang . |
| 5,754,997 | 5/1998 | Lussi et al. . |

FOREIGN PATENT DOCUMENTS 25828   4/1911   (GB) .

*Primary Examiner*—Michael A. Brown
(74) *Attorney, Agent, or Firm*—Robert J. Veal; Christopher A. Holland; Burr & Forman LLP

(57) ABSTRACT

A sterile immobilizing apparatus for restraining the movement of a patient includes a base platform on which is mounted a series of restraining members with a disposable sterile insert member engaging the restraining members and base platform to provide a sanitary surface for performing the desired procedure. The restraining members include a lower back support, an upper back support, an abdominal stabilizer, a cervical stabilizer, and a knee stabilizer. The lower and upper back supports are rigidly mounted to the base platform, while the abdominal stabilizer, cervical stabilizer and knee stabilizer are each movably positioned on the base platform. Between the lower and upper back supports is a lumbar opening in which the sterile insert member is positioned such that the area surrounding the medical procedure performed on the patient is sterile. After the first use, the sterile insert member may then be disposed of as desired the physician and replaced with another sterile insert member for the next procedure.

14 Claims, 5 Drawing Sheets

IMMOBILIZING APPARATUS HAVING A STERILE INSERT

FIELD OF THE INVENTION

The present invention relates to an apparatus for restraining for medical patients. More particularly, the present invention relates to an apparatus for restraining medical patients while providing a sterile field during the performance of a medical procedure, such as a lumbar puncture procedure.

BACKGROUND OF THE INVENTION

A variety of medical procedures require the patient to be restricted in movement. For example, a particular need exists for immobilizing a patient when performing a procedure which requires exact placement and insertion of an invasive needle or probe into the patient's body. This is especially important in medical procedures where the placement of the probe or needle involves the risk of serious injury or damage from an inadvertent motion by the patient. Notable among such procedures are spinal tap or lumbar puncture procedures, involving the insertion of a needle into the spinal canal through the spaces between lumbar vertebrae where any motion of the patient while the needle is being inserted into the body runs a serious risk of spinal damage. Lumbar puncture procedures, which are required for obtaining spinal fluid samples for diagnostic procedures, present a risk of damage to the patient's spinal cord if any movement of the patient occurs during the procedure. Since spinal taps are very uncomfortable, the risk of such motion is particularly severe in children. Moreover, such procedures are done without anesthesia, which compounds the problem of unwanted movement in children. This movement increases the possibility of the puncture instrument contacting the spinal nerves of the patient, thereby causing an involuntary reflex response.

As a result, it is necessary to restrain the patient from moving during the medical procedure. Securing the patient against movement requires that the apparatus positively secure the child against both in response to pain and to involuntary muscle reflex responses. However such restraints cannot be of the type that so bind the child that a panic response ensues, or that unduly heightens the fears of the child.

Various immobilizers have been developed for holding patients, including small children, in a proper position for an operation, such as a spinal tap. One example of such an immobilizer is described in U.S. Pat. No. 5,337,982, in which a pediatric lumbar puncture immobilizer is described having a series of supports mounted thereto to restrain the patient positioned thereon. While the pediatric lumbar puncture immobilizer effectively works to securely restrain the patient in a non-threatening manner, this design does not teach a means for providing a sterile field for the lumbar puncture or "spinal tap" to be performed.

Accordingly, what is needed and is not taught by the prior art is an immobilizing apparatus that provides a sterile field for a physician to perform a medical procedure while restraining the patient from undesired movement that could injure the patient.

SUMMARY OF THE INVENTION

It is an object of the present invention to provide an apparatus that will immobilize a patient to allow a physician to safely operate on the patient.

It is a further object of the present invention to provide an apparatus maintaining a sterile field surrounding the point of the medical procedure performed on the patient.

It is a further object of the present invention to provide a disposable sterile insert member that works in conjunction with a immobilizing apparatus that is easily replaceable to provide a sterile field surrounding the point of the medical procedure performed on the patient.

It is a further object of the present invention to provide a disposable sterile insert member having an attached pair of sterile sheets to maintain a sterile environment around the patient and physician.

These and other objects and advantages of the invention will become apparent from the following detailed description of the preferred embodiment of the invention. The present immobilizing apparatus includes a base platform on which is mounted a series of restraining members, with a disposable sterile insert member provided to engage the restraining members and the base platform to maintain a sterile and hygienic surface for performing the desired medical procedure. The sterile insert member includes a base member with two arm members attached to the ends of the base member. The sterile insert member thereby provides a sterile window surrounded by the base member and arm members to perform the medical procedure. The restraining members include a lower back support, an upper back support, an abdominal stabilizer, a cervical stabilizer, and a knee stabilizer. The lower and upper back supports are fixedly mounted to the base platform, while the abdominal stabilizer, cervical stabilizer and knee stabilizer are each slidably mounted to the base platform to be adjusted to fit each individual patient. Between the lower and upper back supports is a lumbar opening, and the sterile insert member is designed to fit snugly in this lumbar opening. The sterile insert member is thereby positioned between the lower and upper back supports such that a sterile field surrounds the area of the medical procedure to be performed on the patient. After the medical procedure has been performed, the sterile insert member may then be disposed of as desired by the physician and replaced with another sterile insert member for the next medical procedure for the subsequent patient.

In operation, the patient is positioned between the upper and lower support members and the abdominal stabilizer, with the abdominal stabilizer moveable to provide a comfortable yet time restraint of the patient. The cervical and knee stabilizers are further adjusted to provide the desired position for the patient for the medical procedure being performed. Finally, the sterile insert member is inserted between the upper and lower back supports at a position proximate to the area of the patient being operated upon. As a result, the sterile insert member will provide the sterile field surrounding the point of the medical procedure performed on the patient.

BRIEF DESCRIPTION OF THE DRAWINGS

A immobilizing apparatus having a sterile insert embodying features of the invention is described in the accompanying drawings which form a portion of this disclosure and wherein.

DETAILED DESCRIPTION OF THE PREFERRED EMBODIMENT

Figure 1A:
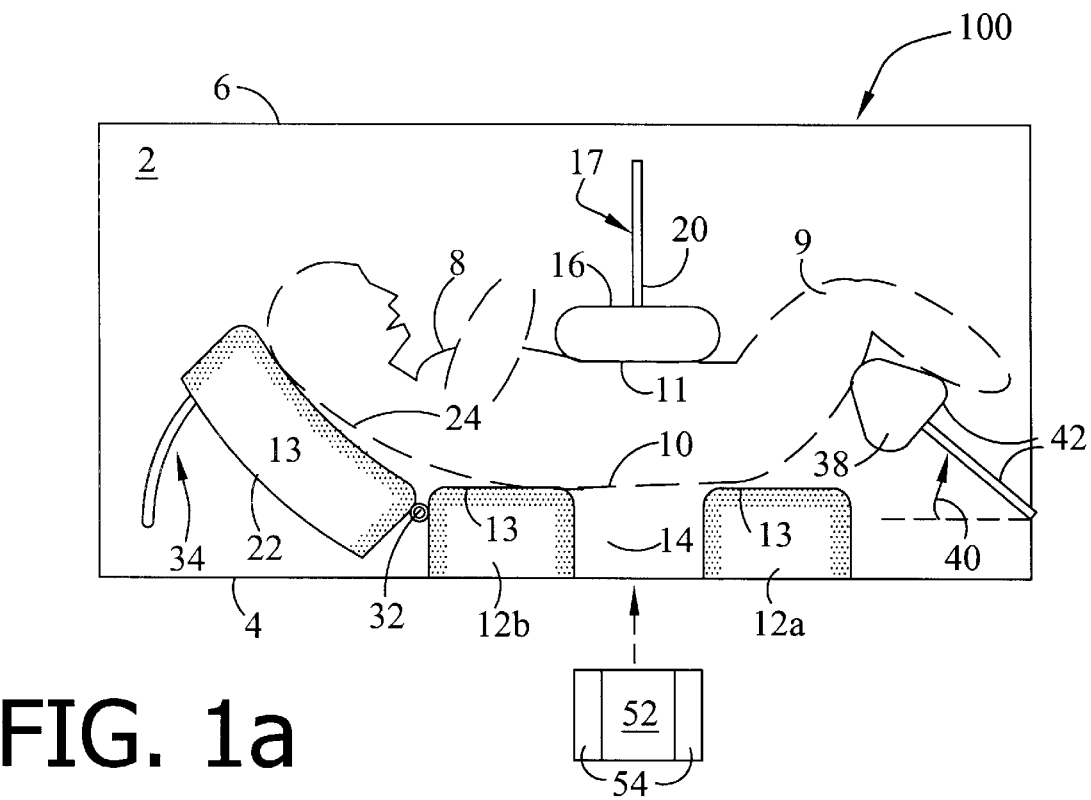
FIG. 1A is a top plan view of the immobilizing apparatus of the present invention, the view illustrating the sterile insert member exploded away from the base platform, the view further illustrating a child in phantom being restrained by the present invention.
Figure 1B:
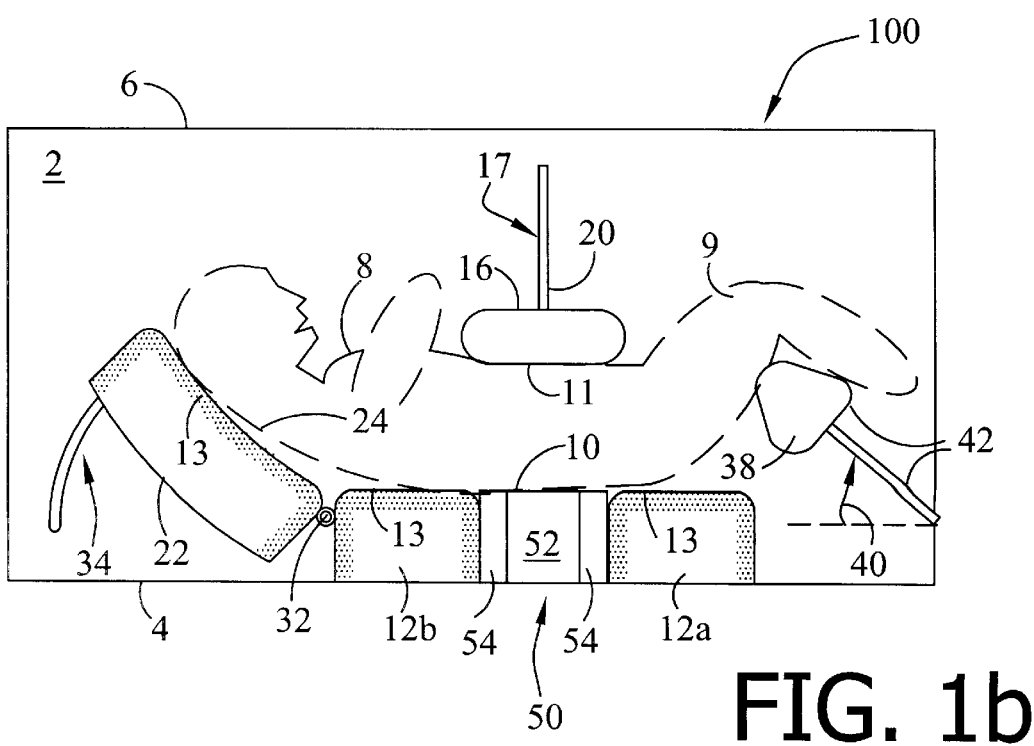
FIG. 1B is a top plan view of the immobilizing apparatus of the present invention as illustrated in FIG. 1A, the view further illustrating the sterile insert member positioned integrally between the upper and lower back supports.
Figure 4:
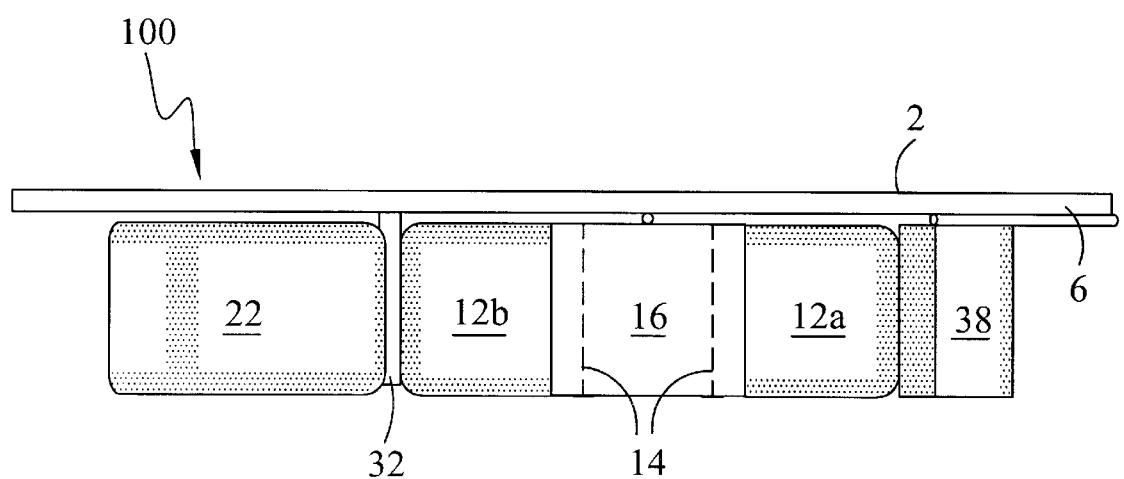
FIG. 4 is a side elevational view of the present invention.

Looking at FIGS. 1A and 1B, the present invention is a immobilizing apparatus 100 that is used to restrain a patient 8, such as a small child, during an invasive medical procedure, such as a spinal tap or other lumbar puncture procedure. The immobilizing apparatus 100 comprises a base platform 2 (preferably a flat board as illustrated in FIG. 4) having a lower surface 4 and an upper surface 6. The base platform 2 preferably has the dimensions required for convenient positioning of the immobilizing apparatus 100 on a conventional operating table (not illustrated). For a small child patient 8, the conventional dimensions of the base platform 2 will be a width of three feet wide and a length of two feet.

Continuing to look at FIG. 1A, the immobilizing apparatus 100 further includes a series of restraining members that are attached to the base platform 2 to restrict the movement of the patient 8. The restraining members include a lower back support 12a, an upper back support 12b, an abdominal stabilizer 16, a cervical stabilizer 22, and a knee stabilizer 38. Looking at FIG. 1B, the immobilizing apparatus 100 further includes a sterile insert member 50 that is positionable between the lower back support 12a and the upper back support 12b. The sterile insert member 50 is operable to maintain a sterile and hygienic field surrounding the point of the medical procedure performed on the patient 8.

The lower back support 12a is perpendicularly mounted toward the lower surface 4 of the base platform 2. The lower back support 12a and upper back support 12b are both preferably padded boards that are wrapped with an impervious, easily cleaned protective covering 13, such as vinyl or leather. The lower back support 12a and upper back support 12b preferably each include a foam pad (not illustrated) within the covering 13 to provide comfort for the patient 8. The collective length of the combination of the lower back support 12a and the upper back support 12b is preferably adapted to support the lower lumbar region 10 of the patient 8 when that patient 8 is positioned on the base platform 2. Between the lower back support 12a and the upper back support 12b is a lumbar opening 14 (see FIG. 1A). The lumbar opening 14 is essentially a rectangular opening that is designed to receive the sterile insert member 50 and provide access by the physician to the inter-vertebra spaces between the third lumbar vertebra down to the fifth lumbar vertebra when the patient 8 is in the position stated above.

Figure 2:
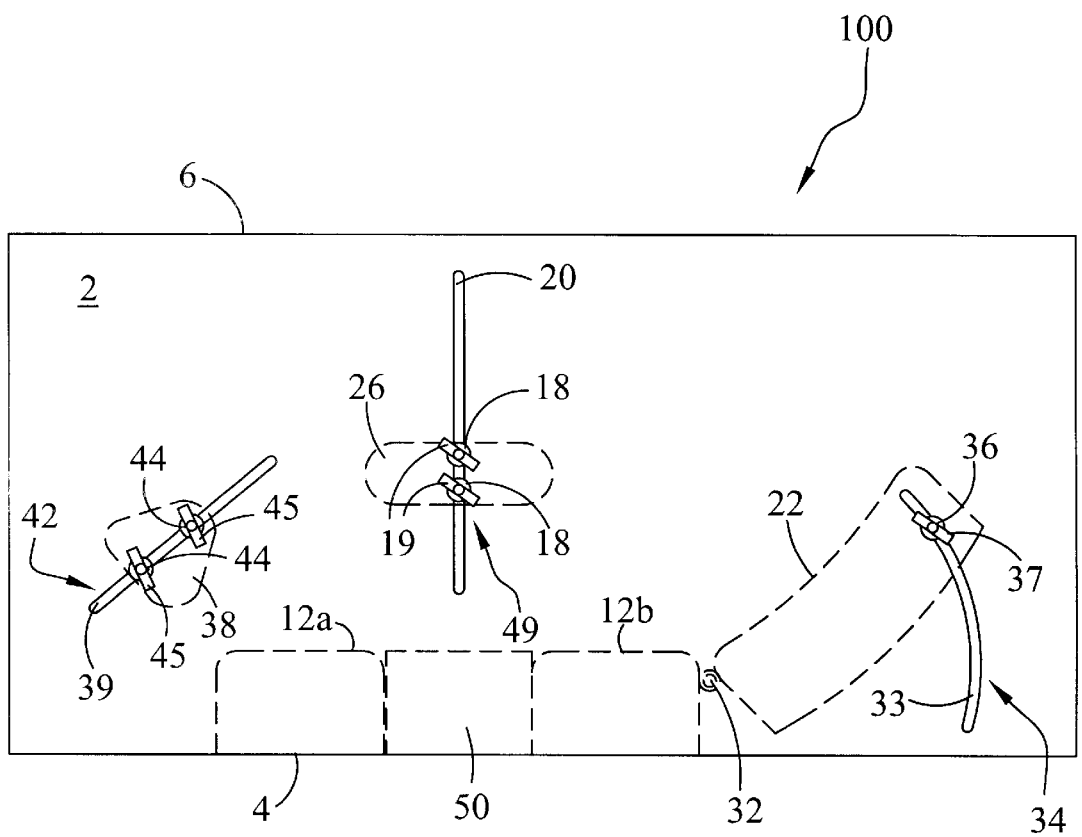
FIG. 2 is a bottom view of the present invention, the restraining members being illustrated in phantom.
Figure 3:
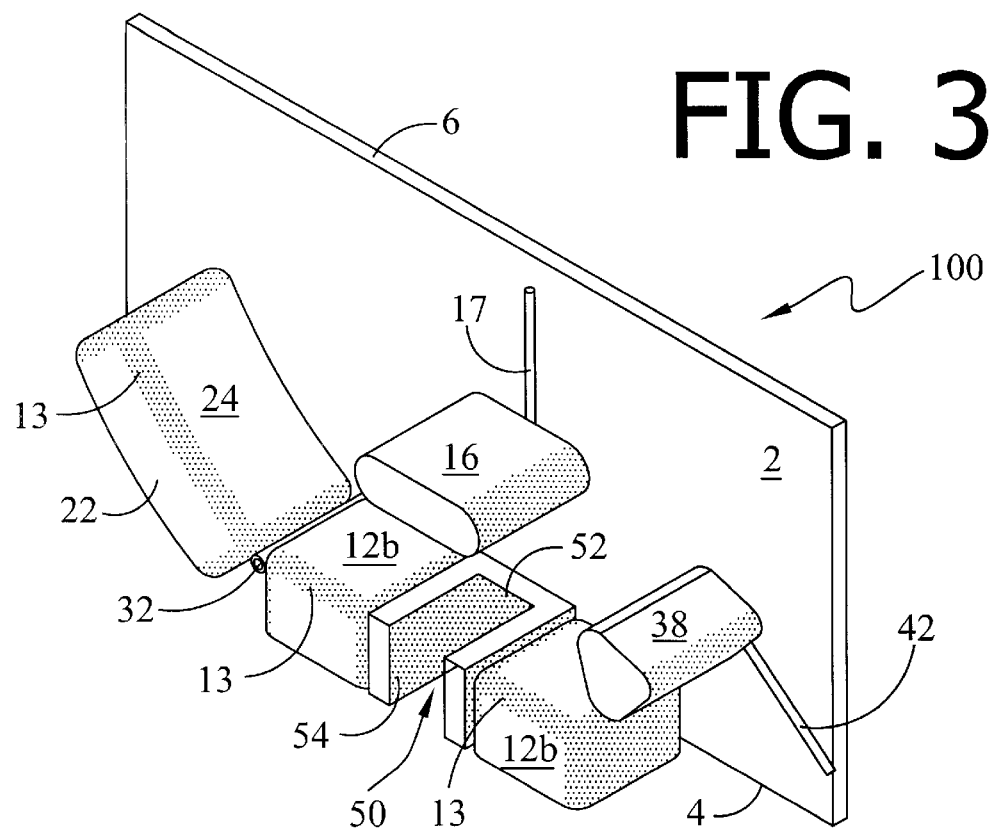
FIG. 3 is a perspective view of the present invention.

Looking at FIGS. 1B, 2, and 3, the sterile insert member 50 is illustrated as employed with the immobilizing apparatus 100. Looking at FIGS. 5, 6A, and 6B, the sterile insert member 50 is more clearly illustrated as a preferably U-shaped member, although other alternative shapes may be implemented in the present invention. The sterile insert member 50 has a base member 52 and a pair of arm members 54 attached to the ends of the base member 52 that extend away from the base member 52 in a perpendicular fashion. The width of the base member 52 is such that the sterile insert member 50 will fit snugly between the first and second back supports 12a, 12b. Additionally, the arm members 54 are attached to the ends of the base member 52 such that the each arm member 54 will firmly contact either the first or second back support 12a, 12b to reinforce the engagement of the sterile insert member 50 between the first and second back supports 12, 12b.

The area between the arm members 54 provides a window defining a sterile area surrounding the area of the patient 8 to be operated upon (see FIG. 1B). The sterile insert member 50 is preferably made of plastic (such as polystyrene or polyethylene) such that the sterile insert member 50 will firmly engage the first and second back supports 12a, 12b. Moreover, another reason explaining why it is desirable that the sterile insert member 50 be made of plastic or a similar material is so that the sterile insert member 50 will be inexpensive for physicians such that the sterile insert member 50 may be disposed of and replaced after each medical procedure performed on the immobilizing apparatus 100. Additionally, the sterile insert member 50 is made of a material that is semi-rigid and able to be sterilized through conventional means before it is provided to the physician for use.

Figure 5:
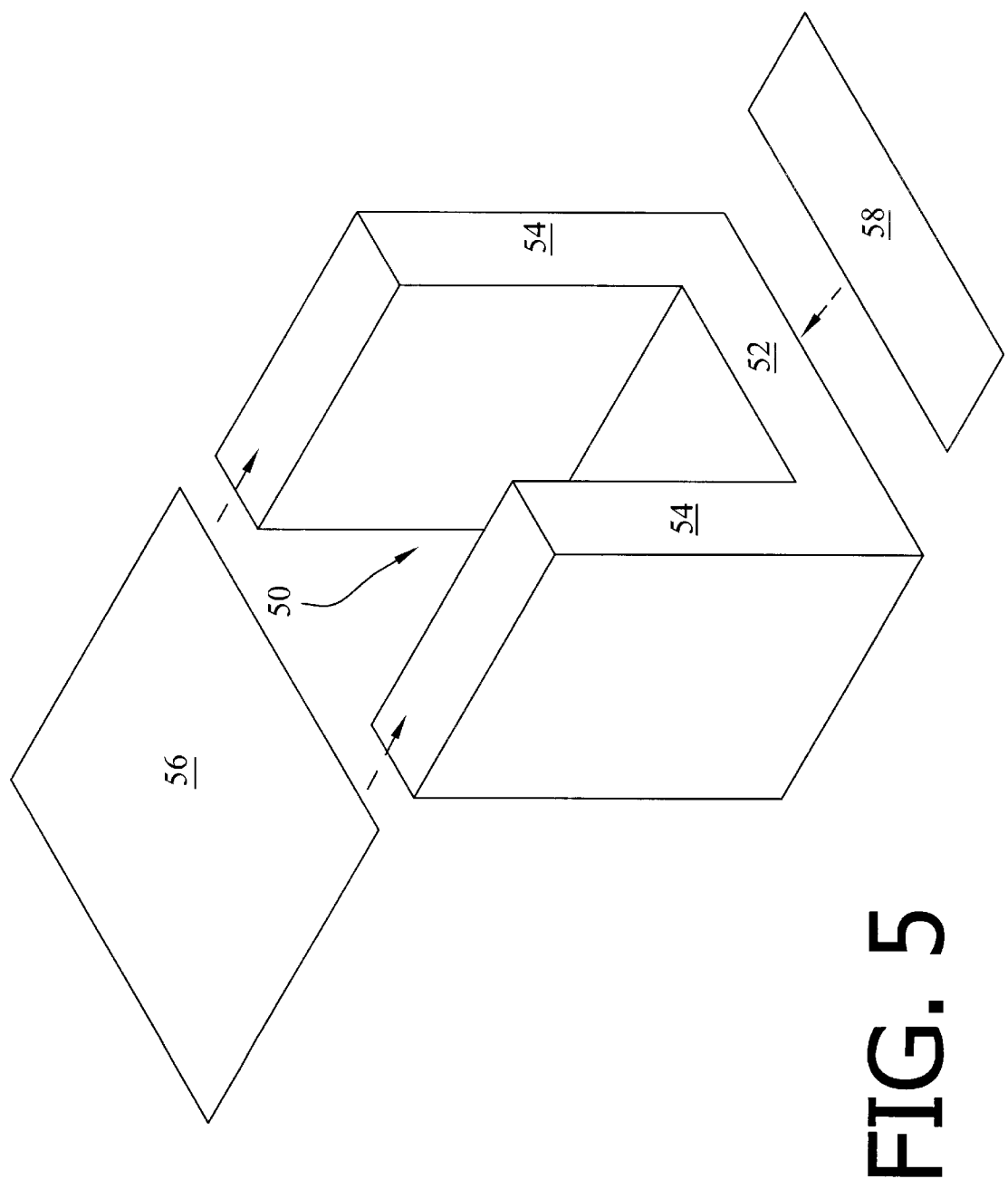
FIG. 5 is a perspective view of the sterile insert member used in the immobilizing apparatus of the present invention.
Figure 6A:
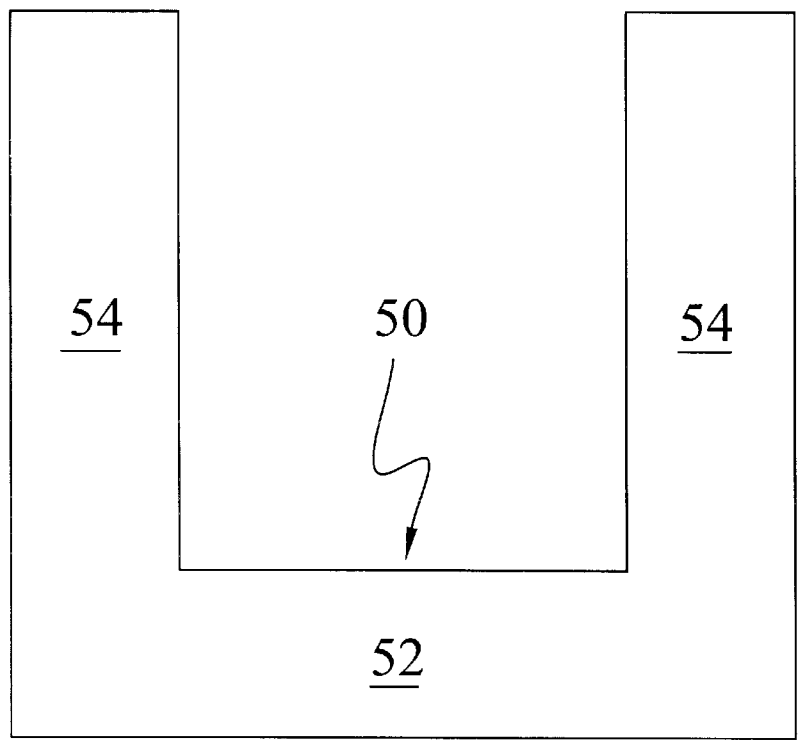
FIG. 6A is a side elevational view of the sterile insert member used in the immobilizing apparatus of the present invention.
Figure 6B:
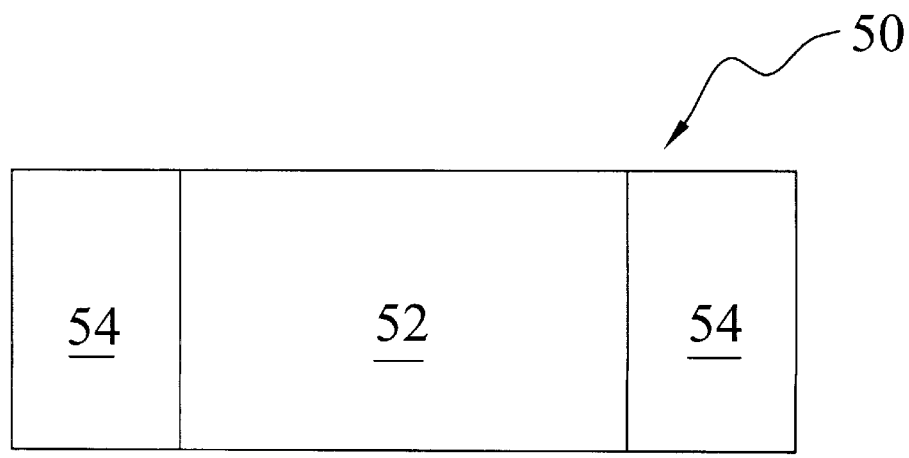
FIG. 6B is a top plan view of the sterile insert member used in the immobilizing apparatus of the present invention.

Looking at FIG. 5, an upper sheet 56 may additionally be attached to the uppermost portion of the arm members 54 to maintain a sterile environment surrounding the patient 8. The upper sheet 56 is provided for use by the physician so that the physician may lay the upper sheet 56 on the patient 8, and thereby extend the sterile field surrounding the area of the medical procedure. Additionally, a lower sheet 58 may also be attached to the bottom surface of the sterile insert member 50. The bottom sheet 58 is provided for use by the physician so that the physician may position the lower sheet 58 toward the physician to further extend the sterile field surrounding the area of medical procedure performed on the patient 8.

Referring back to FIGS. 1A and 1B, the abdominal stabilizer 16, as with the upper and lower back supports 12a, 12b, is mounted to the base platform 2. The abdominal stabilizer 16 is a substantially rectangular or ovular board having a surrounding padding for the comfort of the patient 8. The abdominal stabilizer 16 is mounted to the base platform 2 in a position opposing the lower back support 12a and the upper back support 12b. The abdominal stabilizer 16 is mounted to the base platform 2 via an abdominal positioning means 17 that allows the abdominal stabilizer 16 to be positioned at any location along a line perpendicular to the lower and upper back supports 12a, 12b. This allows the abdominal stabilizer 16 to be moved toward or away from the lower and upper back supports 12a, 12b. The abdominal stabilizer 16 is preferably padded and covered in the same manner as described above for lower and upper back supports 12a, 12b.

Looking at FIG. 2, the abdominal positioning means 17 for the abdominal stabilizer 16 in the preferred embodiment shown comprises a straight abdominal slot or groove 20 that traverses the base platform 2 and extends along the path of desired motion for the abdominal stabilizer 16. Since this path for abdominal stabilizer 16 is into or away from lower and upper back supports 12a, 12b, the abdominal slot 20 is perpendicular to the lower and upper surfaces 4, 6 of the base platform 2. The abdominal stabilizer 16 is secured at any position along the abdominal slot 20 by a locking means 49, which preferably includes one or two threaded abdominal rods 18 and nuts 19. The threaded abdominal rods 18 extend down from the abdominal stabilizer 16 through the abdominal slot 20 and are secured to the base platform 2 by tightening the nuts 19 to the base platform 2. These nuts 19 may preferably be wing nuts, or any form of fastener which is easily tightened by hand.

An alternative abdominal positioning means 17 includes the use of a series of holes (not illustrated) along a line perpendicular to lower surface 4, with the series of holes sized to accept support rods (not illustrated) mounted in the bottom of abdominal stabilizer 16. The support rods can then be positioned by placement is any of the chosen holes as desired. Other abdominal positioning means 17 will naturally occur to the skilled constructor. These means will be suitable for the present invention so long as such means permit ready adjustment of the position of the abdominal stabilizer 16 by the practitioner, and then rigid fixation of the abdominal stabilizer 16 in the position chosen against any possible force exerted by the patient 8.

Referring to FIGS. 1A, 1B and 2, the cervical stabilizer 22 is affixed to the upper back support 12a by a hinged joint 32. The cervical stabilizer 22 preferably has an inward curve 24 for cradling the neck of the patient 8. The cervical stabilizer 22 has a cervical positioning means 34 that positions the cervical stabilizer 22 at any chosen angle with respect to upper back support 12a. The cervical positioning means 34 of the preferred embodiment includes a cervical slot or groove 33 traversing the base platform 2. The cervical slot 33 may be curved or angled as desired by the practitioner, and at least one cervical rod 36 extends down from the cervical stabilizer 22 through the cervical slot 33 to secure the cervical stabilizer 22 against the base platform 2 via a nut 37. As with the abdominal stabilizer 16, the cervical stabilizer 22 has a covered padding 13, and may have many alternative positioning means 34 in addition to the one described in detail above.

Continuing to view FIGS. 1A, 1B, and 2, the knee stabilizer 38 is mounted to the base platform 2 by knee positioning means 42 which permits the knee stabilizer 38 to be moved at an inward angle 40 with respect to lower and upper back supports 12a, 12b. This inward angle 40 results in the knee stabilizer 38 being moveable from a position near the lower surface 4 of the base platform 2 on an inward and upward direction toward the upper surface 6. As with the abdominal stabilizer 16, the knee stabilizer 38 is, in the preferred embodiment, secured to the base platform 2 via a knee positioning means 42 comprising knee rods 44 that extend downwardly from the bottom of the knee stabilizer 38. The knee rods 44 extend down through a knee slot or groove 39 traversing the base platform 2, and the knee rods 44 are secured to the base platform 2 via nuts 45. As with the other retaining members described above, this is only one of several embodiments for constructing the knee positioning means 42.

In operation, as most clearly illustrated in FIGS. 1A and 1B, the patient 8 is positioned on his or her side on the base platform 2 so that the lumbar region 10 of the patient 8 is situated against the lower and upper back supports 12a, 12b. The abdominal stabilizer 16 is then slid along the abdominal slot 20 to be positioned tightly against the abdominal region 11 of the patient 8. This movement thereby positions the patient 8 in abutment between the lower and upper back supports 12a, 12b and the abdominal stabilizer 16. Since all surfaces in contact with the patient 8 are padded, the patient 8 has minimal discomfort from this procedure. The spinal column of the patient 8 is thereby positioned in a stable horizontal and vertical position against the lower and upper back supports 12a, 12b attached to the base platform 2 in conjunction with the clamping pressure exerted by the abdominal stabilizer 16.

Also in the preferred embodiment, the knees 9 of the patient 8 are raised to a near fetal position, bracing the legs against the padded abdominal stabilizer 16, by sliding the knee stabilizer 38 toward the knees 9 to the extent that this movement may comfortably be executed. This positioning of the knee stabilizer 38 serves to stretch the spinal column in preparing for surgery. The full extension of the spinal column for lumbar puncture is accomplished by flexing the upper lumbar and cervical spine forward by positioning the cervical stabilizer 22 at an angle with respect to the lower and upper back supports 12a, 12b. Again, since all of the restraining members are padded, this positioning is performed at a minimal discomfort to the patient 8. However, the resulting position of the patient 8 produces the desired bent spine posture that imparts maximal space between the lumbar vertebra for most efficient and effective insertion of a spinal needle (not illustrated). The window defined by the sterile insert member 50 in the lumbar opening 14 between the lower and upper back supports 12a, 12b provides ready operative access to the L3 to L5 interspaces for lumbar puncture while the patient 8 is fully secured against motion. Moreover, the patient 8 is fully visible to the physician during the procedure, as the immobilizing apparatus 100 does not, unlike prior art supports, conceal the respiration and reaction of the patient 8 from the view of the practitioner.

The immobilizing apparatus 100 will firmly support the patient 8, comfortably positioning the patient 8 in a fashion which is ideal for performing a lumbar puncture procedure. Since the patient 8 is supported laterally by lying on his or her side on the base platform 2, and secured by the clamping effect of the abdominal stabilizer 16 against the lower and upper back supports 12a, 12b, there is good horizontal and vertical alignment of the spinal column. At the same time there is maximal separation of the L3-L4-L5 interspaces for placement of the spinal needle. This separation of the interspaces is created by the locked, angled positioning of the cervical stabilizer 22 which maintains the upper half of the back and the neck in a flexed forward position.

It can readily be seen that the immobilizing apparatus 100, when a patient 8 is positioned for lumbar puncture, with restraining members locked in place, has significant advantages over prior art designs. For example, the sterile insert member 50 provides a sterile environment surrounding the patient to perform the medical procedure that is not found in the prior art. Additionally, the padded and covered restraining members provide a firm but comfortable positioning support for the patient 8. Further, the present invention eliminates the need for one or two nurses to hold the patient 8 during the medical procedure to maintain the stillness of the patient 8. Moreover, the accurate positioning of the spinal column increases the accuracy, ease and efficiency of needle placement and thus of the spinal tap procedure. Most importantly, the danger to an otherwise wiggling or frantic child is reduced by stabilizing the position of that patient 8. In addition, unlike securing devices that essentially fold up a patient 8 and block the physician's view of the patient 8, the physician is able to cleanly observe the respiration and responses of the patient 8 respiration during the entire procedure.

It is to be understood that the form of the IMMOBILIZING APPARATUS HAVING A STERILE INSERT described is a preferred embodiment thereof and that various changes and modifications may be made therein without departing from the spirit of the invention or scope as defined in the following claims.

What is claimed is:

1. An immobilizing apparatus for restraining the movement of a patient during a medical procedure, the immobilizing apparatus comprising:

a base platform;

an upper back support attached to said base platform;

a lower back support attached to said base platform;

a cervical stabilizer attached to said base platform, said cervical stabilizer pivotally connected to one end of said upper back support and linearly moveable upon said base platform;

an abdominal stabilizer mounted to said base platform opposite said upper and lower back supports, wherein said abdominal stabilizer is linearly moveable upon said base platform to secure the patient between said abdominal stabilizer and said upper and lower back supports; and a sterile insert member detachably affixed between said upper back support and said lower back support to provide a sterile field proximate the patient.

2. The immobilizing apparatus as described in claim 1 wherein said sterile insert member comprises:

a base member having a first and second end;

a first arm member connected to said first end of said base member; and a second arm member connected to said second end of said base member.

3. The immobilizing apparatus as described in claim 1 wherein said sterile insert member comprises a semi-rigid material.

4. The immobilizing apparatus as described in claim 1 further comprising a knee stabilizer slidably attached to said base platform to engage a knee of the patient.

5. The immobilizing apparatus as described in claim 4 comprising means for positioning said knee stabilizer, said knee positioning means including:

a knee slot traversing said base platform; and a knee rod attached to said knee stabilizer;

wherein said knee rod slidably engages said knee slot to move said knee stabilizer along the direction of said knee slot.

6. The immobilizing apparatus as described in claim 1 further comprising means for positioning said abdominal stabilizer, said abdominal positioning means including:

an abdominal slot traversing said base platform; and a abdominal rod attached to said abdominal stabilizer;

wherein said abdominal rod slidably engages said abdominal slot to move said abdominal stabilizer along the direction of said abdominal slot.

7. The immobilizing apparatus as described in claim 1 further comprising means for positioning said cervical stabilizer, said cervical positioning means including:

a cervical slot traversing said base platform; and a cervical rod attached to said cervical stabilizer;

wherein said cervical rod slidably engages said cervical slot to move said abdominal stabilizer along the direction of said abdominal slot.

8. The immobilizing apparatus as described in claim 7 wherein said cervical slot is arcuate.

9. In an immobilizing apparatus for restraining a person during a lumbar puncture medical procedure having a lower back support, an upper back support, a cervical support and an abdominal support mounted to a base platform to support and restrain movement of the person, wherein the improvement comprises a sterile insert member detachably affixed between the upper back support and the lower back support to provide a sterile field surrounding the person.

10. The immobilizing apparatus as described in claim 9 wherein the sterile insert member comprises:

a base member having a first and second end;

a first arm perpendicularly connected to said first end of said base member; and a second arm perpendicularly connected to said second end of said base member, such that said first arm, said second arm, and said base member form a window for access to the patient;

wherein said first arm abuts said upper back support and said second arm abuts said lower back support.

11. An immobilizer for positioning a patient for lumbar puncture comprising:

a base platform having a first surface and a second surface;

an upper back support and a lower back support extending from said first surface of said base platform, the distance between said upper back support and said lower back support defining a lumbar opening;

a sterile insert member detachably affixed between said upper back support and said lower back support in said lumbar opening;

a cervical stabilizer slidably engaging said base platform and pivotally attached to said upper back support such that said cervical stabilizer may rotate to support the patient;

an abdominal stabilizer slidably attached to said base platform opposing said upper and lower back supports to engage the patient such that the patient abuts said abdominal stabilizer and said upper and lower back supports.

12. The immobilizer as described in claim 11 wherein said sterile insert member comprises a base member and a first and second arm member, said first and second arm members being attached to opposing ends of said base member to form a window for access to the patient.

13. The immobilizing apparatus as described in claim 11 wherein said sterile insert member is made of a pliable material.

14. The immobilizing apparatus as described in claim 11 further comprising a knee stabilizer slidably attached to said base platform to engage a knee of the patient.

* * * * *